United States Patent
Satou et al.

(10) Patent No.: US 11,040,720 B2
(45) Date of Patent: Jun. 22, 2021

(54) SLEEPINESS LEVEL PREDICTION DEVICE AND SLEEPINESS LEVEL PREDICTION METHOD

(71) Applicants: Marelli Corporation, Saitama (JP); National University Corporation Tokyo University of Agriculture and Technology, Fuchu (JP)

(72) Inventors: Haruhiko Satou, Saitama (JP); Horomasa Miura, Saitama (JP); Shuang Wu, Saitama (JP); Hiroshi Mouri, Fuchu (JP); Soya Aoki, Fuchu (JP)

(73) Assignees: Marelli Corporation, Saitama (JP); University Corporation Tokyo University Of Agriculture And Technology, Tokyo (JP)

( * ) Notice: Subject to any disclaimer, the term of this patent is extended or adjusted under 35 U.S.C. 154(b) by 0 days.

(21) Appl. No.: 16/753,381

(22) PCT Filed: Oct. 3, 2018

(86) PCT No.: PCT/JP2018/037096
§ 371 (c)(1),
(2) Date: Apr. 3, 2020

(87) PCT Pub. No.: WO2019/069999
PCT Pub. Date: Apr. 11, 2019

(65) Prior Publication Data
US 2020/0276978 A1 Sep. 3, 2020

(30) Foreign Application Priority Data
Oct. 6, 2017 (JP) .............................. JP2017-196301

(51) Int. Cl.
*B60W 40/08* (2012.01)
*B60W 40/09* (2012.01)
(Continued)

(52) U.S. Cl.
CPC ............ *B60W 40/09* (2013.01); *B60W 40/02* (2013.01); *B60W 40/08* (2013.01);
(Continued)

(58) Field of Classification Search
CPC .......... G08B 21/06; G08B 31/00; A61B 5/18; A61B 5/16; B60K 28/06; B60K 28/066;
(Continued)

(56) References Cited

U.S. PATENT DOCUMENTS 4,928,090 A 5/1990 Yoshimi et al.
6,335,689 B1 1/2002 Mine
(Continued)

FOREIGN PATENT DOCUMENTS

JP 01-250221 A 10/1989
JP 2000-185575 A 7/2000
(Continued)

*Primary Examiner* — Benyam Haile
(74) *Attorney, Agent, or Firm* — Global IP Counselors, LLP (57) ABSTRACT

A sleepiness level prediction device includes a vehicle information acquisition unit, a driver information acquisition unit, and a control unit. The vehicle information acquisition unit is configured to acquire information relating to a vehicle. The driver information acquisition unit is configured to acquire information relating to a driver. The control unit is configured to calculate a stimulus amount to be given to the driver based on a current driving load of the driver and a driving load after a prescribed time, based on the information relating to the vehicle, calculate a non-acclimation degree indicative of a level at which the driver is not acclimated to driving based on a change in the stimulus (Continued)

amount, and predict a sleepiness level of the driver after the prescribed time based on a current sleepiness level of the driver estimated based on the information relating to the driver and the non-acclimation degree.

9 Claims, 7 Drawing Sheets

(51) Int. Cl.
  *B60W 40/02* (2006.01)
  *G08B 21/06* (2006.01)
  *G08B 31/00* (2006.01)
(52) U.S. Cl.
  CPC . *B60W 2040/0827* (2013.01); *B60W 2540/22* (2013.01); *B60W 2540/229* (2020.02); *B60W 2556/10* (2020.02); *G08B 21/06* (2013.01); *G08B 31/00* (2013.01)
(58) Field of Classification Search
  CPC ... B60W 40/09; B60W 40/08; B60W 40/0818
  See application file for complete search history.

(56) References Cited

U.S. PATENT DOCUMENTS

| | | | |
|---|---|---|---|
| 2003/0043045 | A1 | 3/2003 | Yasushi et al. |
| 2011/0043350 | A1* | 2/2011 | Ben David ............ B60Q 9/00 340/441 |
| 2014/0046546 | A1 | 2/2014 | Kollegger et al. |
| 2017/0020432 | A1* | 1/2017 | Kusukame ............ A61B 5/024 |
| 2017/0365101 | A1* | 12/2017 | Samec .................... A61B 3/09 |
| 2018/0060732 | A1* | 3/2018 | Yuan ....................... G06N 5/02 |

FOREIGN PATENT DOCUMENTS

| | | |
|---|---|---|
| JP | 2003-061939 A | 3/2003 |
| JP | 2008-228759 A | 10/2008 |
| JP | 2009-157606 A | 7/2009 |
| JP | 2010-134608 A | 6/2010 |
| JP | 2010-140358 A | 6/2010 |
| JP | 2017-127616 A | 7/2017 |
| WO | 2014/167811 A1 | 10/2014 |

* cited by examiner

SLEEPINESS LEVEL PREDICTION DEVICE AND SLEEPINESS LEVEL PREDICTION METHOD

CROSS-REFERENCE TO RELATED APPLICATION

This is a U.S. national phase application of PCT/JP2018/037096, filed on Mar. 10, 2018, which claims priority to Japanese Patent Application 2017-196301 filed in Japan on Oct. 6, 2017. The entire disclosure of Japanese Patent Application 2017-196301 is incorporated herein by reference.

TECHNICAL FIELD

The present invention relates to a sleepiness level prediction device and a sleepiness level prediction method.

BACKGROUND ART

From the past, developments have advanced for a driving assistance device for estimating the sleepiness level of a driver to prevent falling asleep at the wheel, etc.

A detection device disclosed in Japanese Laid-Open Patent Publication No. 2010-134608 detects the opening and closing degree and the direction of the line of sight of the driver indicating the eye opening status of the driver, and determines the opening and closing of the eyes of the driver.

SUMMARY

A driver needs to maintain an awake state of a fixed level or greater during driving. In automatic driving as well, for example when switching from automatic driving to manual driving, it is necessary for the driver to maintain an awake state at a level at which it is possible to perform manual driving. To have the driver maintain the awake state, an external stimulus such as a temperature or olfactory stimulus, etc., is given to the driver, for example. However, there are cases when it takes time until the suppression effect of sleepiness in the driver by this kind of external stimulus is exhibited. Therefore, it is necessary to predict in advance the sleepiness level of the driver after a prescribed time.

The purpose of the present invention, which was created considering the kind of problem noted above, is to provide a sleepiness level prediction device and a sleepiness level prediction method that can accurately predict in advance the sleepiness level of the driver.

A sleepiness level prediction device of an embodiment includes: a vehicle information acquisition unit that acquires information relating to a vehicle; a driver information acquisition unit that acquires information relating to a driver; and a control unit that calculates a stimulus amount to be given to the driver based on the current driving load of the driver and the driving load after a prescribed time, based on the acquired information relating to the vehicle, calculates a non-acclimation degree showing the level at which the driver is not acclimated to driving based on the change in the calculated stimulus amount, and predicts a sleepiness level of the driver after the prescribed time based on a current sleepiness level of the driver estimated based on the acquired information relating to the driver and the calculated non-acclimation degree.

A sleepiness level prediction method of an embodiment includes: acquiring information relating to a vehicle; acquiring information relating to a driver; calculating a stimulus amount given to the driver based on the current driving load of the driver and the driving load after a prescribed time, based on the acquired information relating to the vehicle, and for calculating a non-acclimation degree showing the level at which the driver is not acclimated to driving based on the change in the calculated stimulus amount; and predicting a sleepiness level of the driver after the prescribed time based on a current sleepiness level of the driver estimated based on the acquired information relating to the driver and the calculated non-acclimation degree.

With the sleepiness level prediction device and the sleepiness level prediction method of an embodiment of the present invention, it is possible to accurately predict in advance the sleepiness level of a driver.

DETAILED DESCRIPTION OF EMBODIMENTS

Hereafter, an embodiment of the present invention is explained while referring to drawings.

A sleepiness level prediction device 1 of an embodiment calculates a non-acclimation degree H of a driver based on acquired information relating to a vehicle. The sleepiness level prediction device 1 predicts a future sleepiness level $D_1$ of the driver based on a current sleepiness level $D_0$ of the driver estimated based on acquired information relating to the driver and the calculated non-acclimation degree H. The future sleepiness level $D_1$ corresponds to the sleepiness level $D_1$ after a prescribed time as noted in the claims. Hereafter, when not distinguishing between the driver's current sleepiness level $D_0$ and the future sleepiness level $D_1$, both are noted collectively as sleepiness level D.

Figure 1:
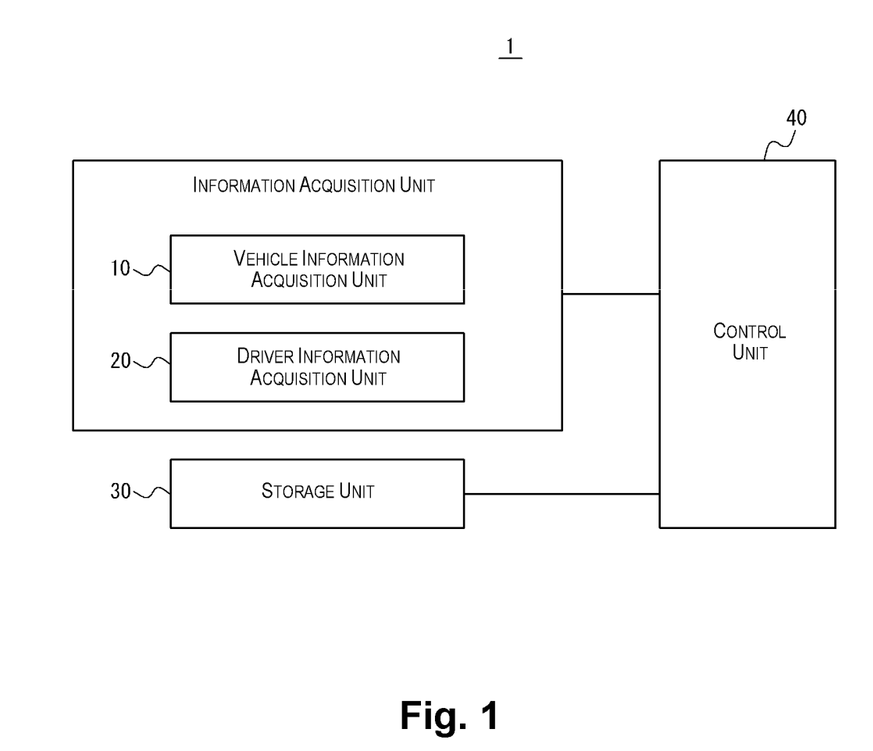
FIG. 1 is a block diagram showing the configuration of a sleepiness level prediction device of an embodiment.

FIG. 1 is a block diagram showing the configuration of the sleepiness level prediction device 1 of the embodiment. The sleepiness level prediction device 1 has: an information acquisition unit configured by a vehicle information acquisition unit 10 and a driver information acquisition unit 20; a storage unit 30; and a control unit 40.

The vehicle information acquisition unit 10 includes, for example, a camera, LIDAR (Light Detection And Ranging), radar, or an appropriate sensor such as a speed sensor or a steering angle sensor, etc. The vehicle information acquisition unit 10 may also include appropriate devices configuring a car navigation system, for example. The vehicle information acquisition unit 10 may also include appropriate devices configuring an advanced driver assistance system (ADAS), for example. The vehicle information acquisition unit 10 may also include appropriate devices configuring an in-vehicle infotainment (IVI: In-Vehicle Infotainment) system, for example. The vehicle information acquisition unit 10 may also include appropriate devices configuring an automatic driving system, for example. The vehicle information acquisition unit 10 may also include appropriate devices connected to, for example, a controller area network (CAN) which is one communication system in an in-vehicle network. The vehicle information acquisition unit 10 may also include appropriate devices for performing vehicle-to-vehicle and road-to-vehicle communication (V2X), for example.

The vehicle information acquisition unit 10 acquires information relating to the vehicle. As described hereafter, information relating to the vehicle includes, for example, information relating to changes in the traveling environment of the vehicle, information relating to the vehicle state, and information relating to the host vehicle position status.

The information relating to changes in the traveling environment of the vehicle includes, for example, information relating to changes in the traffic participant status such as the characteristics, position, or moving speed, etc., of the traffic participants. The information relating to changes in the traveling environment of the vehicle includes, for example, information relating to road conditions such as the status of the road surface, the distance from the white line of the road, the road type, or the number of lanes, etc., or to changes in signal status. Information relating to changes in the traveling environment of the vehicle includes, for example, information relating to changes in the front vehicle status, rear vehicle status, parallel travel vehicle status, or crossing vehicle status. Information relating to changes in the traveling environment of the vehicle includes, for example, information relating to changes in communication status with an outside network, status of a moving body in the surrounding air, or POI (Point Of Interest). Information relating to changes in the traveling environment of the vehicle includes, for example, information relating to the destination and the planned route to that destination.

Information relating to the vehicle state includes, for example, information relating to the speed of the vehicle, the accelerator state, the brake state, the clutch state, the blinker state, the gear state, the wiper state, the door mirror state, the seat state, the audio state, the warning state, the light state, the steering state, the idle state, the air conditioner state, the seatbelt state, or the driving operation level.

The information relating to the host vehicle position status includes, for example, information relating to the current position of the host vehicle shown by the vehicle latitude, longitude, altitude, slope, or travel lane position, etc. The information relating to the host vehicle position status includes, for example, information relating to the temperature, humidity, weather, brightness, or clarity in the current position of the host vehicle.

The driver information acquisition unit 20 includes a camera or an appropriate sensor such as a wearable sensor, etc., for example. The driver information acquisition unit 20 may also include appropriate sensors connected to the CAN, for example. The driver information acquisition unit 20 acquires information relating to the driver. As explained hereafter, information relating to the driver includes, for example, information relating to the state of the driving behavior of the driver, and information relating to the state of the driver.

The information relating to the driving behavior of the driver includes, for example, information relating to the driver's accelerator operation, brake operation, clutch operation, blinker operation, gear operation, wiper operation, door mirror operation, seat operation, audio operation, light operation, steering operation, air conditioner operation, or seatbelt operation. The information relating to the driving behavior of the driver includes, for example, information relating to speed adjustment, maintaining of the travel lane, front confirmation, rear confirmation, side confirmation, object tracking, front scan, or side scan.

The information relating to the state of the driver includes, for example, information relating to the biological state, face direction, line of sight, blinking state, body movement, excitement level, level of feeling moved, sense of fun, satisfaction level, emotion, request content, driving (riding) duration, visibility, glare, ease of hearing, or utterance content. Here, the biological state of the driver includes, for example, brain waves, cerebral blood flow, blood pressure, blood sugar level, amino acids in blood, HbA1c, γ-GPT, household medicine blood concentration, heart rate, body temperature, body sensed temperature, hunger sensation, tiredness.

The driver information acquisition unit 20 is explained as acquiring the abovementioned information relating to the driver, but the invention is not limited to this. The driver information acquisition unit 20 may also acquire the same information relating to a passenger.

The abovementioned information acquired by the information acquisition unit configured by the vehicle information acquisition unit 10 and the driver information acquisition unit 20 is outputted to the control unit 40, and stored in the storage unit 30 as necessary.

The storage unit 30 includes, for example, semiconductor memory or magnetic memory. The storage unit 30 is not limited to these, and may include any storage device. The storage unit 30 may include an optical storage device such as an optical disk, for example, or may include a magneto-optical disk, etc. The storage unit 30 stores as necessary the various types of information noted above acquired from the control unit 40. The storage unit 30 stores a program, etc., executed by the control unit 40 to operate the sleepiness level prediction device 1. The storage unit 30 stores as necessary the various types of data such as calculation results, etc., by the control unit 40. The storage unit 30 may also function as work memory when the control unit 40 is operating.

The control unit 40 includes a processor for controlling and managing the overall sleepiness level prediction device 1, starting with each function block of the sleepiness level prediction device 1, for example. The control unit 40 includes a processor such as a CPU (Central Processing Unit) that executes the program that defines control procedures, for example. This kind of program is stored in the storage unit 30, for example.

Figure 2:
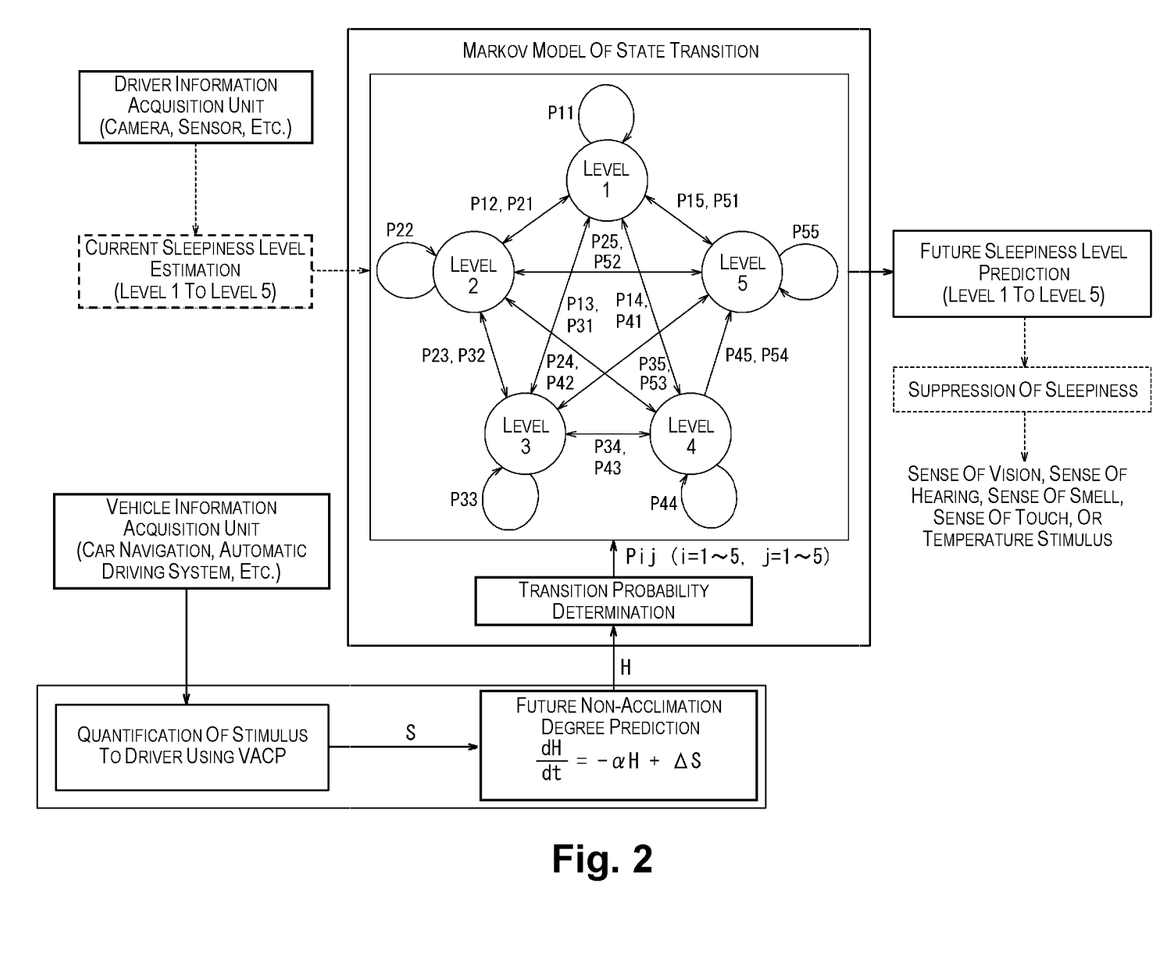
FIG. 2 is a schematic diagram showing the process executed by a control unit of the sleepiness level prediction device of FIG. 1.

FIG. 2 is a schematic diagram showing the processing executed by the control unit 40 of the sleepiness level prediction device 1 of FIG. 1. Referring to FIG. 2, a detailed explanation is given regarding the processing of the control unit 40 for realizing the function of the sleepiness level prediction device 1 for predicting the future sleepiness level $D_1$ of the driver.

The control unit 40 calculates a change $\Delta S$ in a stimulus amount S given to the driver based on the information relating to the vehicle acquired by the vehicle information acquisition unit 10. The calculation method of the stimulus amount S, for example, is based on a method of applying to the driving behavior of the driver who is driving the vehicle an index called VACP that quantitatively estimates the cognitive resources needed for each type of operation for estimating the work load of a pilot at the aircraft design stage, for example. The stimulus amount S given to the driver, interpreted as corresponding to the driving load amount applied to the driver, for example, is calculated based on the VACP value applied to the driving behavior of the driver. In this way, the stimulus amount S is quantified using VACP applied to the driving behavior of the driver.

VACP, in a state with human behavior divided into four elements of sense of vision (V: Visual), sense of hearing (A: Auditory), recognition (C: Cognitive), and mind (P: Psychomotor), is an index represented by a numerical value of 1.0 to 7.0 according to the amount of cognitive resources consumed. The amount of cognitive resources consumed is defined using a paired comparison method investigation.

TABLE 1

| Scale | Definition |
| --- | --- |
| | Visual (V) |
| 1.0 | Visually registered/image detected |
| 3.7 | Visually distinguished |
| 4.0 | Visually inspected/checked |
| 5.0 | Visually positioned/arrayed |
| 5.4 | Visually tracked/followed |
| 5.9 | Visually read (code) |
| 7.0 | Visually scanned/searched, monitored |
| | Auditory (A) |
| 1.0 | Sound detected/registered |
| 2.0 | Sound orientation (generally) |
| 4.2 | Sound orientation (selectively) |
| 4.3 | Auditory feedback confirmed |
| 4.9 | Meaning content interpreted (speech) |
| 6.6 | Sound features distinguished |
| 7.0 | Sound pattern interpreted |
| | Cognitive (C) |
| 1.0 | Automatically (simple association) |
| 1.2 | Selection of alternative choice |
| 3.7 | Code/signal confirmation |
| 4.6 | Evaluation/judgment (simple aspect examined) |
| 5.3 | Coding/decoding, recall |
| 6.8 | Evaluation/judgment (several aspects examined) |
| 7.0 | Estimate, calculate, convert |
| | Psychomotor (P) |
| 1.0 | Speech |
| 2.2 | Discrete operation (button, toggle, trigger) |
| 2.6 | Continuous adjustment |
| 4.6 | Operative |
| 5.8 | Discrete adjustment |
| 6.5 | Symbolic production (writing) |

TABLE 1-continued

| Scale | Definition |
| --- | --- |
| 7.0 | Serial discrete operation (keyboard input) |

The VACP values relating to the driving behavior of the driver driving the vehicle are estimated as shown in Table 2 below, for example, based on the conventional VACP values noted in Table 1. Based on this, the control unit 40 calculates the VACP value applied to the driving behavior of the driver. The control unit 40 can objectively determine the driving load amount for each driver. The control unit 40 determines that the driving load amount of the driver is small if the VACP is low, and determines that the driving load amount of the driver is large if the VACP is high.

TABLE 2

| Driving Behavior | Visual | Auditory | Cognitive | Psychomotor |
| --- | --- | --- | --- | --- |
| Speed adjustment | 0.0 | 0.0 | 1.0 | 2.6 |
| Travel lane maintenance | 0.0 | 0.0 | 1.0 | 2.6 |
| Front confirmation | 4.0 | 0.0 | 1.0 | 0.0 |
| Rear confirmation | 4.0 | 0.0 | 1.0 | 0.0 |
| Side confirmation | 7.0 | 0.0 | 1.0 | 0.0 |
| Object tracking | 4.0 | 0.0 | 1.0 | 0.0 |
| Front scan | 7.0 | 0.0 | 3.7 | 0.0 |
| Rear scan | 7.0 | 0.0 | 3.7 | 0.0 |

The control unit 40 acquires from the vehicle information acquisition unit 10, for example, information relating to a planned route from a destination set using a car navigation system by the driver, etc., to that destination. The control unit 40 predicts the driving behavior of the driver from the present until after a prescribed time based on acquired information relating to the planned route, and calculates the VACP value of the driver from the present until after the prescribed time. The prescribed time includes the time from implementation of sleepiness elimination control by the vehicle until a suppression effect of sleepiness of the driver is exhibited. The sleepiness elimination control by the vehicle includes, for example, temperature control using an air conditioner with cool air from the air conditioner facing the driver's face, etc., or smell control, etc., such as generating an aroma from any device. In this way, the prescribed time includes the time until the suppression effect of sleepiness of the driver by an external stimulus such as temperature or olfactory stimulus, etc., for example, is exhibited. The control unit 40, for example, determines that the driving behavior of the driver that is doing visual recognition of the front traveling environment corresponds to "front confirmation" in Table 2 to monitor automatic driving, adds the 4.0 relating to "sense of vision" and the 1.0 relating to "recognition" and calculates the VACP value as 5.0.

The control unit 40 calculates the stimulus amount S given to the driver from the present until after the prescribed time based on the VACP value of the driver from the present until after the prescribed time calculated based on the acquired information relating to the planned route. More specifically, the control unit 40 calculates the ratio of the maximum value based on the calculated VACP value, respectively, and calculates the stimulus amount S as a value of 0 to 1.0. As the maximum value of VACP, for example, the VACP value calculated in a state with a large load applied to the driver is adopted. As an example, the maximum value of VACP may be 80 calculated when driving on a narrow road with a high difficulty level.

The control unit 40 calculates the non-acclimation degree H using formula 1 based on the change ΔS of the stimulus amount S for each calculated time from the present until after the prescribed time. The control unit 40 predicts the future non-acclimation degree H using formula 1. In formula 1, a is a coefficient.

[Formula 1]

$$dH/dt = -\alpha H + \Delta S \qquad \text{(formula 1)}$$

The non-acclimation degree H shows the level to which the driver is not acclimated to changes in the stimulus given from outside during driving. The control unit 40 determines that the driver is not acclimated to the changes in stimulus when the non-acclimation degree H is high, and determines that the driver is acclimated to the changes in stimulus when the non-acclimation degree H is low. The control unit 40 sets the value of the non-acclimation degree H to 1, for example, in an initial state when the driver is not acclimated to changes in stimulus.

Referring to formula 1, the non-acclimation degree H has first order lag characteristics with respect to the change ΔS in the stimulus amount S. As is described later, the non-acclimation degree H shows characteristics such as of the change amount of the non-acclimation degree H becoming gradually smaller as time passes while decreasing by the time constant 1/α.

The control unit 40 predicts the future sleepiness level $D_1$ of the driver based on the Markov model of state transition that depends on the non-acclimation degree H for which a transition probability Pij, in which the current sleepiness level $D_0$ of the driver transitions to a prescribed future sleepiness level $D_1$, is calculated using the abovementioned method.

More specifically, the control unit 40 estimates the current sleepiness level $D_0$ of the driver based on information relating to the driver acquired from the driver information acquisition unit 20. The control unit 40, for example, calculates a feature quantity of the eyes of the driver such as the eyelid opening rate or the eyelid opening and closing speed, etc., from a face image of the driver taken using a camera, and estimates the current sleepiness level $D_0$ of the driver by using a histogram of a prescribed time relating to the feature quantity of the eyes. The estimating method of the current sleepiness level $D_0$ of the driver by the control unit 40 is not limited to this, and any method may be used. For example, the control unit 40 may also estimate the current sleepiness level $D_0$ of the driver by judging opening and closing of the eyes of the driver by detecting the eyelid opening rate of the driver and the direction of the line of sight of the driver.

The sleepiness level D of the driver is estimated in five levels from level 1 to level 5, for example. The control unit 40 determines that the larger the numerical value of the sleepiness level D as the level rises, the more that sleepiness of the driver is promoted. The control unit 40 determines that the smaller the numerical value of the sleepiness level D as the level falls, the more the sleepiness of the driver is suppressed. Level 1 corresponds to "Not sleepy at all," for example. Level 2 corresponds to "Somewhat sleepy," for example. Level 3 corresponds to "Sleepy," for example. Level 4 corresponds to "Quite sleepy," for example. Level 5 corresponds to "Very sleepy," for example. The method of dividing the levels using the numerical value of the sleepiness level D is not limited to the description above. The control unit 40 may also divide the levels of the sleepiness level D using any number and any contents.

The control unit 40 determines the transition probability Pij of transitioning from the current sleepiness level $D_0$ of the driver to a prescribed future sleepiness level $D_1$ based on the non-acclimation degree H calculated using formula 1. i shows each level value of the current sleepiness level $D_0$ of the driver. j shows each level value of the future sleepiness level $D_1$ of the driver. i and j change the value taken according to the number of level divisions. When the sleepiness level D of the driver is estimated using five levels from level 1 to level 5, each of i and j take a value from 1 to 5. The control unit 40 determines the transition probability Pij by comparing the non-acclimation degree H calculated using formula 1 and data relating to the transition probability Pij for each value of the non-acclimation degree H, for example. The data relating to the transition probability Pij for each value of the non-acclimation degree H, for example, is acquired beforehand by experimentation, and stored in advance in the storage unit 30.

The control unit 40 predicts the future sleepiness level $D_1$ of the driver using the transition probability Pij determined based on the non-acclimation degree H and the current sleepiness level $D_0$ of the driver. The control unit 40 adopts as the future sleepiness level $D_1$ of the driver a level value with the highest transition probability Pij, for example. The control unit 40 performs optional measures for suppressing sleepiness of the driver when the future sleepiness level $D_1$ of the driver is higher than a prescribed value, and the awake state of the driver is predicted to decrease after a prescribed time. The prescribed value may be determined in advance by the manufacturer of the sleepiness level prediction device 1, or may be determined as needed by the user such as the driver, etc. Optional measures include giving an external stimulus to the driver, for example. The control unit 40 controls optional in-vehicle equipment to give an external stimulus such as a sense of vision, sense of hearing, sense of smell, sense of touch, or temperature stimulus, etc., to the driver, for example.

In this way, the control unit 40 uniquely determines the future sleepiness level $D_1$ of the driver with the level value for which the transition probability Pij is the highest, and performs optional measures for suppressing sleepiness based on the determined future sleepiness level $D_1$. The method for performing measures is not limited to this and may be any method. The control unit 40 may also perform optional measures when the probability for which the level value of the predicted future sleepiness level $D_1$ is 3 or greater is higher than the prescribed value, for example. The prescribed value in this case may be determined in advance by the manufacturer of the sleepiness level prediction device 1, or may be set as necessary by the user such as the driver, etc.

The control unit 40 predicts the future sleepiness level $D_1$ of the driver using the kind of method described above. The control unit 40 may also update the transition probability Pij by comparing the future sleepiness level $D_1$ of the driver predicted in the past with the current sleepiness level $D_0$ of the driver estimated in real time based on information relating to the driver acquired by the driver information acquisition unit 20. The control unit 40 may also determine whether these two sleepiness levels D match. When the control unit 40 determines that the two sleepiness levels D match, the transition probability Pij is maintained, whereas when determined that the two sleepiness levels D do not match, the transition probability Pij is updated so that they match.

Following, a detailed explanation is given of the results of verification through experimentation of the behavior of each parameter at each of the abovementioned processing stages.

Figure 3:
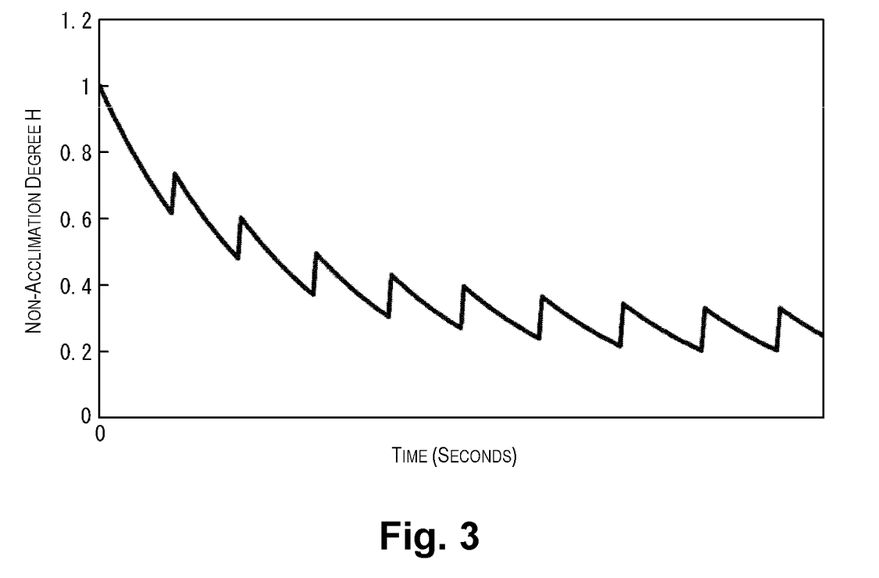
FIG. 3 is a drawing showing an example of a time change of a non-acclimation degree calculated based on formula 1.
Figure 4:
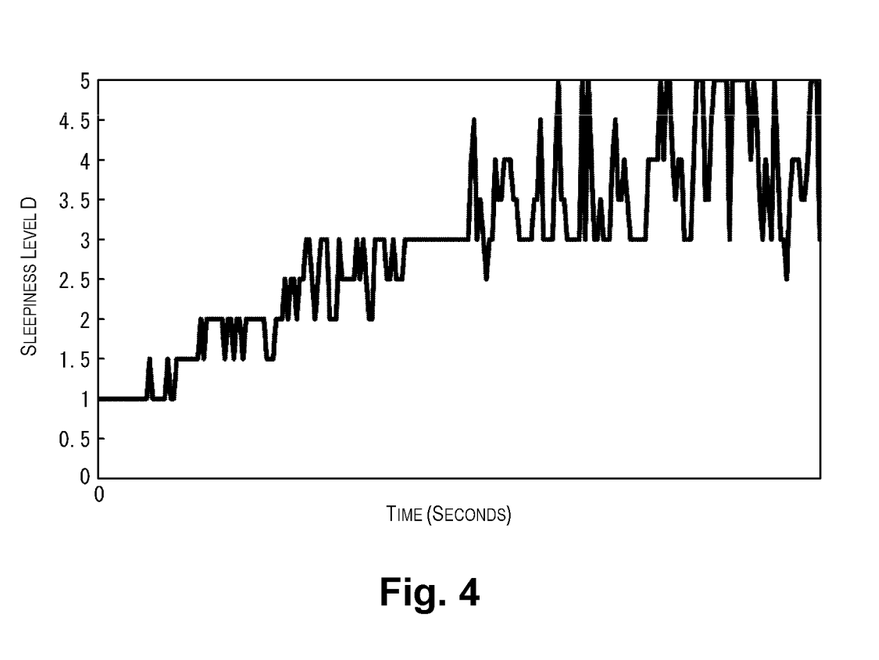
FIG. 4 is a drawing showing an example of a time change of the estimated value of the sleepiness level.

FIG. 3 is a drawing showing an example of time changes of the non-acclimation degree H calculated based on formula 1. The non-acclimation degree H in FIG. 3 shows the value calculated under the condition of giving a prescribed driving load to the driver once each prescribed time. FIG. 4 is a drawing showing an example of time changes of the estimated value of the sleepiness level D. The sleepiness level D in FIG. 4 shows the actually estimated value using the driver information acquisition unit 20 correlated to the time changes of the non-acclimation degree H of FIG. 3. The sleepiness level D in FIG. 4 has levels divided by 0.5 each in 9 stages from 1 to 5. FIG. 3 and FIG. 4 show the results acquired together with the same trial. The time of the horizontal axis of FIG. 3 and FIG. 4 correspond to each other, and should be understood as showing the same scale and the same absolute value.

Referring to FIG. 3, the non-acclimation degree H shows characteristics such as the change amount of the non-acclimation degree H gradually becoming smaller as time elapses while decreasing by the time constant $1/\alpha$. The change $\Delta S$ of the stimulus amount S increases by the prescribed driving load given to the driver once each prescribed time, so the non-acclimation degree H increases each time and shows a sawtooth shaped waveform.

Referring to FIG. 3 and FIG. 4, the sleepiness level D has a tendency to gradually increase while repeating short increases and decreases conversely to the non-acclimation degree H. In this way, we can see that the non-acclimation degree H and the sleepiness level D have a negative correlation. When the non-acclimation degree H is high and the driver is not acclimated to the changes in stimulus, the sleepiness level D is low. Conversely, when the non-acclimation degree H is low and the driver is acclimated to changes in stimulus, the sleepiness level D is high.

Figure 5:
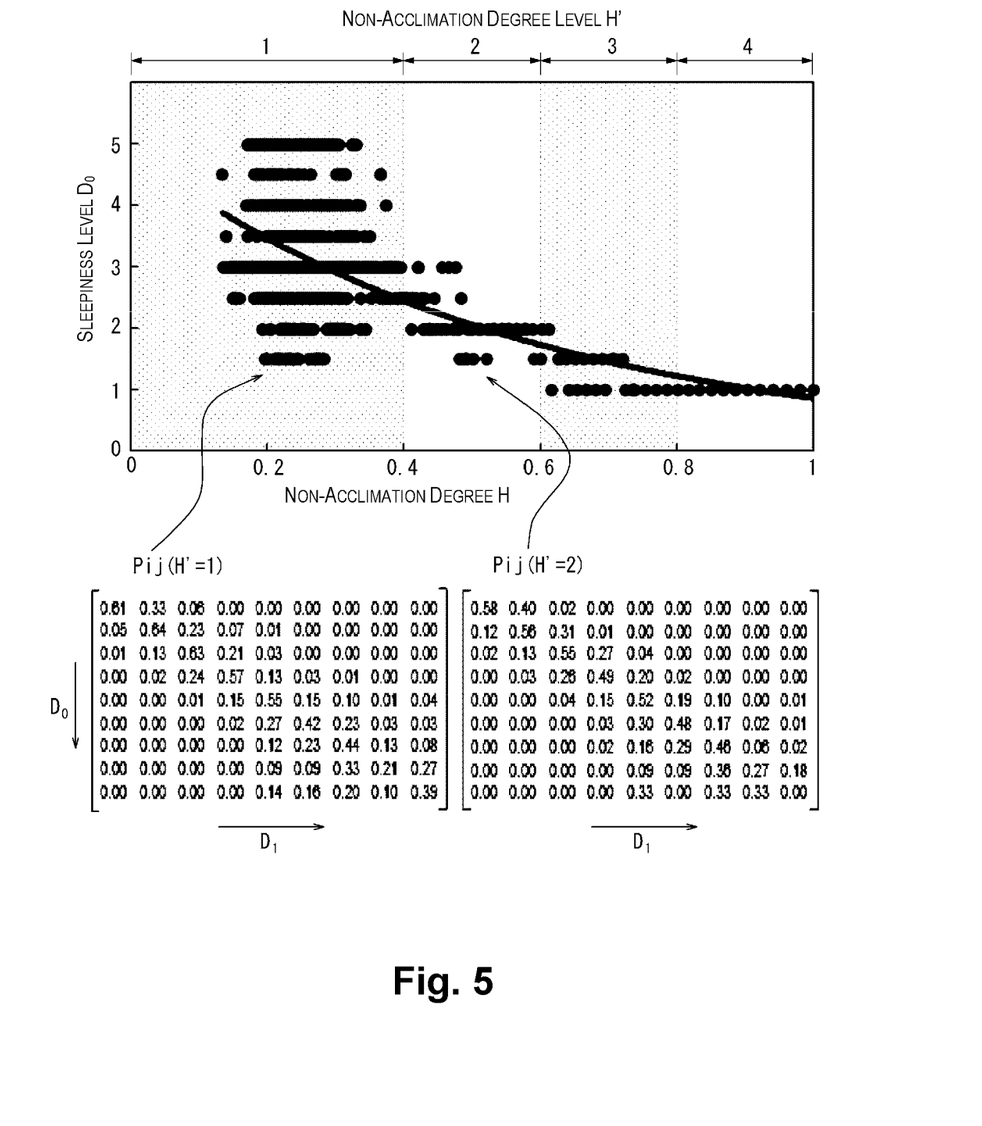
FIG. 5 is a drawing showing an example of data relating to transition probability.

FIG. 5 is a drawing showing an example of data relating to the transition probability Pij. The upper part of FIG. 5 shows the state with plotting by points of the relationship of the non-acclimation degree H and the current sleepiness level $D_0$ of the driver. The vertical axis shows the current sleepiness level $D_0$ of the driver. The horizontal axis shows the non-acclimation degree H. The lower part of FIG. 5 shows an example of the value of each transition probability Pij determined for each level of the non-acclimation degree H. The row of the rows and columns shown in the lower part of FIG. 5 shows level i of the current sleepiness level $D_0$, and the column shows the level j of the future sleepiness level $D_1$.

Referring to FIG. 5, the sleepiness level D is divided in levels of 0.5 each at nine levels from 1 to 5. Therefore, for the rows and columns of the transition probability Pij, there are 9×9 rows and columns. When determining the transition probability Pij for each value of the non-acclimation degree H by experimentation in advance, the non-acclimation degree H can be divided into any number of levels in a range from 0 to 1, for example. The non-acclimation degree H can be divided into four non-acclimation degree levels H', for example. The transition probability Pij is determined for each non-acclimation degree level H'. The lower part of FIG. 5 shows as an example only the value of each transition probability Pij when the value of the non-acclimation degree level H' is 1 or 2.

Figure 6:
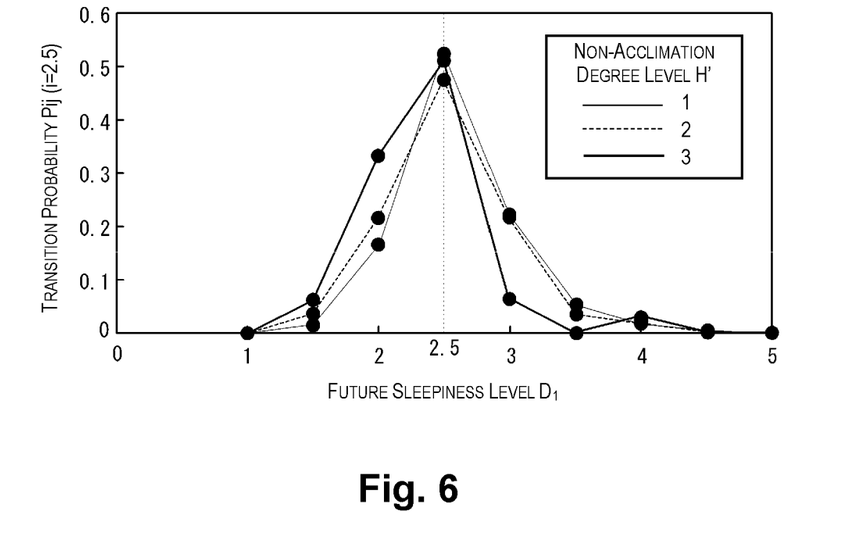
FIG. 6 is a drawing showing a transition probability value for each non-acclimation degree level.

FIG. 6 is a drawing showing the value of the transition probability Pij for each non-acclimation degree level H'. FIG. 6 is a drawing that shows with a graph the value of the transition probability Pij (i=2.5) for each of the future sleepiness levels $D_1$ transitioning after a prescribed time with the level value of the current sleepiness level $D_0$ as 2.5. FIG. 6 shows the value of the transition probability Pij (i—2.5) for three non-acclimation degree levels 1, 2, 3.

Referring to FIG. 6, when the level value of the non-acclimation degree level H' is 3, in other words, when the driver is not acclimated to changes in the stimulus from outside, the probability of the future sleepiness level $D_1$ transitioning to level 2 is high compared to when the level value of the non-acclimation degree level H' is 1, 2. When the driver is not acclimated to changes in the stimulus from the outside, it is easier to transition to a state with more suppression of sleepiness.

Figure 7:
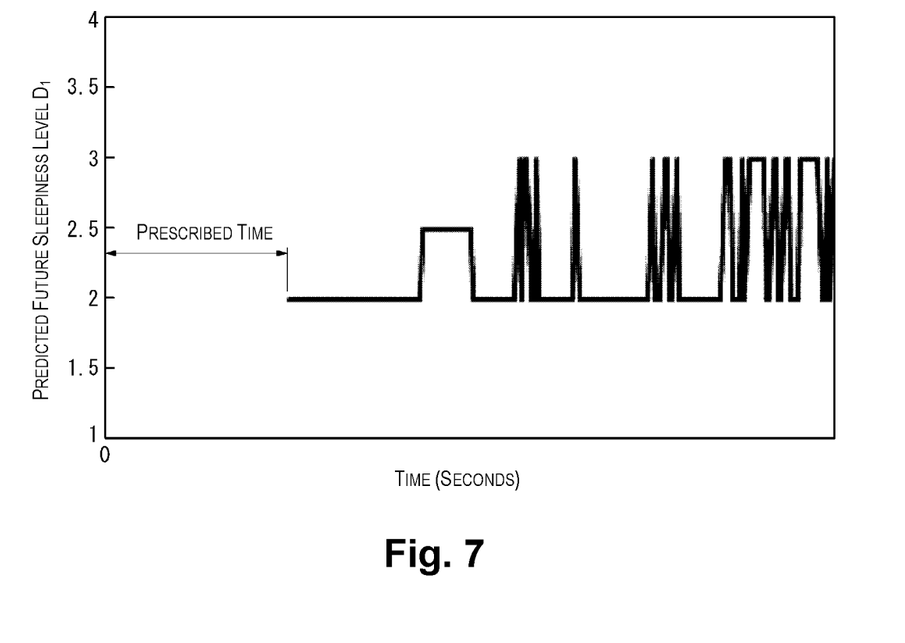
FIG. 7 is a drawing showing a time change of the future sleepiness level predicted using the sleepiness level prediction device of FIG. 1.
Figure 8:
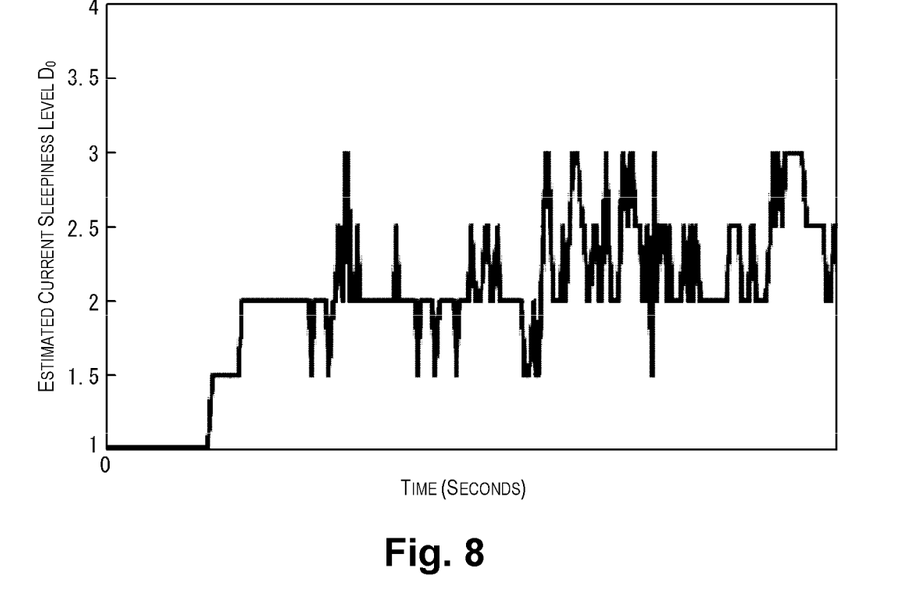
FIG. 8 is a drawing showing a time change of the current sleepiness level actually estimated using the sleepiness level prediction device of FIG. 1.

FIG. 7 is a drawing showing the time changes of the future sleepiness level $D_1$ predicted by the sleepiness level prediction device 1 of FIG. 1. The vertical axis of FIG. 7 shows the future sleepiness level $D_1$ for which the transition probability Pij for transitioning after a prescribed time is highest. FIG. 8 is a drawing showing the time changes of the current sleepiness level $D_0$ actually estimated by the sleepiness level prediction device 1 of FIG. 1. The time of the horizontal axis of FIG. 7 and FIG. 8 correspond to each other, and should be understood as showing the same scale and the same absolute value.

Referring to FIG. 7, the start point of data relating to predicted future sleepiness level $D_1$ is after the prescribed time. The future sleepiness level $D_1$ at that start point shows the level value predicted at time 0 seconds which is the start point of data relating to the current sleepiness level $D_0$ of FIG. 8. When FIG. 7 and FIG. 8 are compared, we can interpret that though each timing is slightly different with sleepiness level 2 as a base, the tendency to swing mainly upward is correct.

Figure 9:
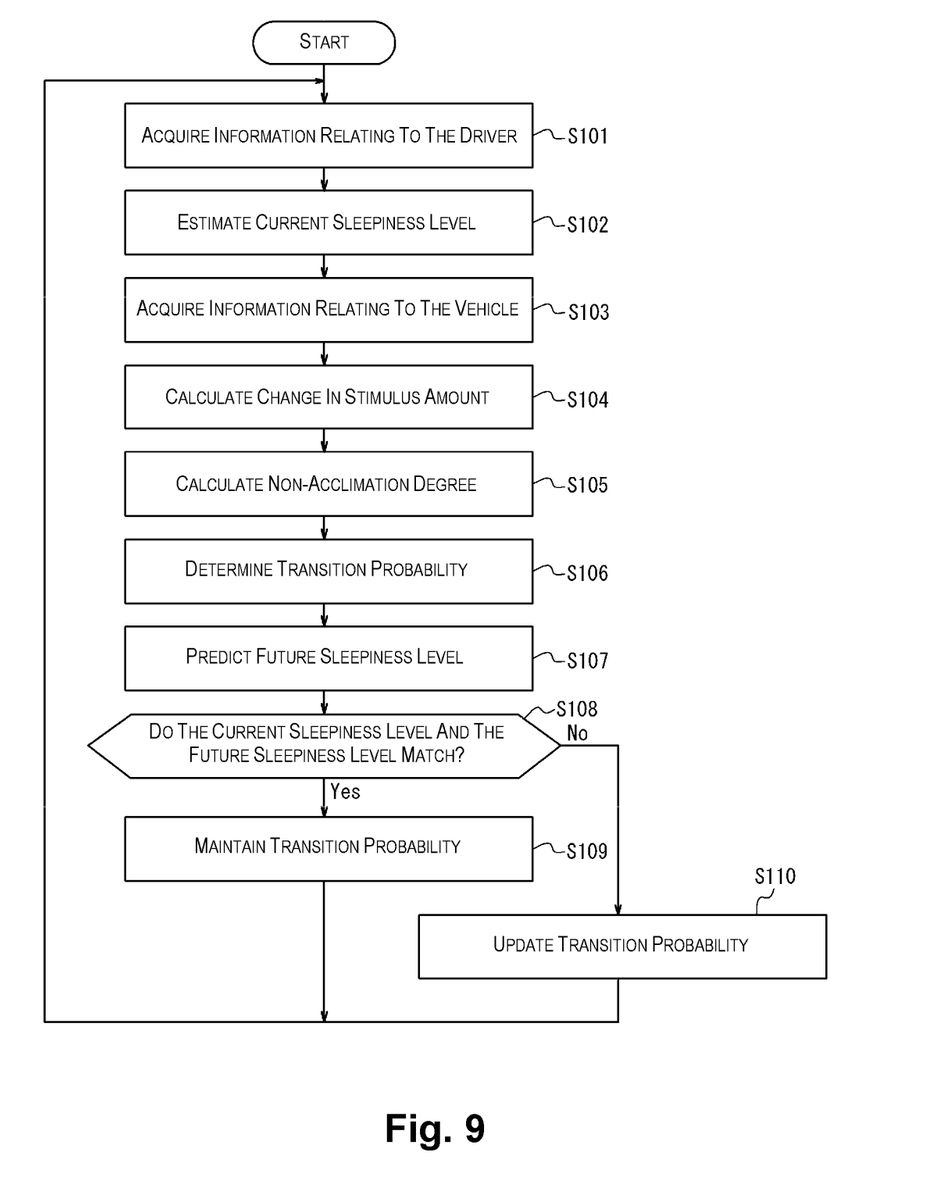
FIG. 9 is a flow chart showing the operation of the sleepiness level prediction device of FIG. 1.

FIG. 9 is a flow chart showing the operation of the sleepiness level prediction device 1 of FIG. 1. Referring to FIG. 9, the flow of the processing of the control unit 40 to realize the function of the sleepiness level prediction device 1 of predicting the future sleepiness level $D_1$ of the driver is explained.

The control unit 40 acquires information relating to the driver from the driver information acquisition unit 20 (step S101).

The control unit 40 estimates the current sleepiness level $D_0$ of the driver based on the acquired information relating to the driver (step S102).

The control unit 40 acquires the information relating to the vehicle from the vehicle information acquisition unit 10 (step S103).

The control unit 40 calculates the change $\Delta S$ of the stimulus amount S given to the driver based on the acquired information relating to the vehicle (step S104).

The control unit 40 calculates the non-acclimation degree H based on the calculated change $\Delta S$ of the stimulus amount S (step S105).

The control unit 40 determines the transition probability Pij based on the non-acclimation degree H calculated using formula 1 (step S106).

The control unit 40 predicts the future sleepiness level $D_1$ of the driver based on the estimated current sleepiness level $D_0$ of the driver and the determined transition probability Pij (step S107).

The control unit 40 determines whether the future sleepiness level $D_1$ of the driver predicted in the past and the current sleepiness level $D_0$ of the driver estimated in real time match (step S108). When the control unit 40 determines that the two sleepiness levels D match, the process advances to step S109. When the control unit 40 determines that the two sleepiness levels D do not match, the process advances to step S110.

When the control unit 40 determines that the two sleepiness levels D match, the transition probability Pij is maintained (step S109).

When the control unit 40 determines that the two sleepiness levels D do not match, the transition probability Pij is updated (step S110).

The control unit 40 returns to step S101 and repeats the same flow again.

The sleepiness level prediction device 1 of the embodiment like that noted above can accurately predict in advance the sleepiness level D of the driver. The sleepiness level prediction device 1 can objectively quantify the non-acclimation degree H that has a negative correlation with the sleepiness level D by calculating the non-acclimation degree H of the driver based on the acquired information relation to the vehicle. By predicting the future sleepiness level $D_1$ of the driver based on the current sleepiness level $D_0$ of the driver and the calculated non-acclimation degree H, the sleepiness level prediction device 1 can accurately predict the change from the current sleepiness level $D_0$ by predicting the state relating to future acclimation of the driver. Therefore, the sleepiness level prediction device 1 can perform measures that will suppress sleepiness of the driver with optimal timing. The sleepiness level prediction device 1 can exhibit the maximum effect of suppressing sleepiness of the driver by performing these kinds of measures in advance.

The sleepiness level prediction device 1 can flexibly handle calculation of the non-acclimation degree H according to the planned route set by the driver, for example, by calculating the non-acclimation degree H of the driver based on the information relating to changes in the traveling environment of the vehicle. The sleepiness level prediction device 1 can accurately calculate the non-acclimation degree H of the driver corresponding to the current and future actual traveling environment. As a result, the sleepiness level prediction device 1 can predict the future sleepiness level $D_1$ of the driver more accurately.

The sleepiness level prediction device 1 can objectively quantify the driving load accompanying the driving behavior of the driver by calculating the driving load amount of the driver based on the information relating to changes in the traveling environment of the vehicle.

The sleepiness level prediction device 1 can objectively quantify the stimulus amount S given to the driver by calculating the change $\Delta S$ of the stimulus amount S given to the driver. The sleepiness level prediction device 1 can calculate the non-acclimation degree H more accurately to match the driver status by calculating the non-acclimation degree H based on the calculated change $\Delta S$ of the stimulus amount S. As a result, it is possible for the sleepiness level prediction device 1 to predict the future sleepiness level $D_1$ of the driver more accurately. For example, by the sleepiness level prediction device 1 calculating the stimulus amount S using VACP, it is possible to objectively quantify the driving load accompanying driving behavior of the driver and to accurately calculate the stimulus amount S given to the driver.

The sleepiness level prediction device 1 can easily calculate the non-acclimation degree H by using the formula 1 having first order lag characteristics with respect to the change $\Delta S$ of the stimulus amount S.

The sleepiness level prediction device 1 can accurately predict the future sleepiness level $D_1$ of the driver even in a case when the variation of the sleepiness level D with respect to the prescribed non-acclimation degree H is large by using a state transition model in which the transition probability Pij depends on the calculated non-acclimation degree H. By stochastically predicting the sleepiness level D based on the non-acclimation degree H, the sleepiness level prediction device 1 can suppress a decrease in the prediction accuracy due to variation of the sleepiness level D with respect to the prescribed non-acclimation degree H compared to a case of uniquely predicting the sleepiness level D.

The sleepiness level prediction device 1 can accurately predict the sleepiness level D in a state suited to each driver by updating the transition probability Pij when determined that the future sleepiness level $D_1$ and the current sleepiness level $D_0$ do not match. When the prediction target is changed to a new driver, the sleepiness level prediction device 1 can update the transition probability Pij that was suited to the original driver before changing to be suitable for the new driver. The sleepiness level prediction device 1 is capable of customizing for each driver.

The present invention was explained based on the various drawings and embodiments, but it should be noted that a person skilled in the art can easily perform various modifications and revisions based on the present disclosure. Therefore, please note that these modifications or revisions are included within the scope of the present invention. For example, it is possible to rearrange each means or the function, etc., included in each step, etc., so as not to be in logical conflict, and it is possible to combine a plurality of means or steps, etc. into one, or to divide them.

As an embodiment of the present invention, the sleepiness level prediction device 1 was mainly explained, but the present invention can also be realized as a sleepiness level prediction method substantially equivalent to the sleepiness level prediction device 1 described above. The present invention can also be realized as a program for executing the sleepiness level prediction method on a computer. These should also be understood as items within the scope of the present invention.

The sleepiness level prediction device 1 was explained as calculating the non-acclimation degree H of the driver based on information relating to changes in the traveling environment of the vehicle. The calculation method of the non-acclimation degree H is not limited to this. The sleepiness level prediction device 1 may also calculate the non-acclimation degree H of the driver based on any information relating to the vehicle acquired by the vehicle information acquisition unit 10.

The sleepiness level prediction device 1 was explained as calculating the VACP and the change $\Delta S$ of the stimulus amount S based on information relating to changes in the traveling environment of the vehicle, and calculating the non-acclimation degree H. The calculation method of the non-acclimation degree H is not limited to this. The sleepiness level prediction device 1 may also calculate the non-acclimation degree H directly using only the information relating to changes in the traveling environment of the vehicle, or may calculation the non-acclimation degree H using another suitable method. The sleepiness level prediction device 1 may also predict the future sleepiness level $D_1$ directly using only the information relating to changes in the traveling environment of the vehicle.

The sleepiness level prediction device 1 was explained as calculating the non-acclimation degree H of the driver based on information relating to the vehicle acquired by the vehicle information acquisition unit 10. The calculation method of the non-acclimation degree H is not limited to this. The sleepiness level prediction device 1 may also calculate the non-acclimation degree H of the driver based on information relating to the driver acquired using the driver information acquisition unit 20 in addition to the information relating to the vehicle acquired using the vehicle information acquisition unit 10.

The sleepiness level prediction device 1 was explained as calculating the non-acclimation degree H using the formula 1 having first order lag characteristics with respect to the change ΔS of the stimulus amount S. The calculation method of the non-acclimation degree H is not limited to this. The sleepiness level prediction device 1 may also calculate the non-acclimation degree H based on the stimulus amount S using another suitable method.

The sleepiness level prediction device 1 was explained as predicting the future sleepiness level $D_1$ of the driver based on the state transition model in which the transition probability Pij is dependent on the calculated non-acclimation degree H. The prediction method for the future sleepiness level $D_1$ is not limited to this. The sleepiness level prediction device 1 may also predict the future sleepiness level $D_1$ of the driver with any method that does not use this kind of state transition model as long as the calculated non-acclimation degree H and the sleepiness level D correspond accurately.

Explanation of Codes

1: Sleepiness level prediction device; 10: Vehicle information acquisition unit; 20: Driver information acquisition unit; 30: Storage unit; and 40: Control unit.

The invention claimed is:

1. A sleepiness level prediction device comprising:
    a vehicle information acquisition unit configured to acquire information relating to a vehicle;
    a driver information acquisition unit configured to acquire information relating to a driver; and
    a control unit configured to
        calculate a change in a stimulus amount to be given to the driver, the change in the stimulus amount being a difference between a current stimulus amount determined based on a current driving load of the driver and a predicted stimulus amount after a prescribed time determined based on a predicted driving load after the prescribed time, the predicted driving load being predicted based on the information relating to the vehicle acquired by the vehicle information acquisition unit,
        calculate a non-acclimation degree indicative of a level at which the driver is not acclimated to driving based on the change in the stimulus amount calculated, and
        predict a sleepiness level of the driver after the prescribed time based on a current sleepiness level of the driver estimated based on the information relating to the driver acquired by the driver information acquisition unit and the non-acclimation degree calculated.

2. The sleepiness level prediction device of claim 1, wherein the vehicle information acquisition unit is configured to acquire information relating to changes in a traveling environment of the vehicle as the information relating to the vehicle.

3. The sleepiness level prediction device of claim 2, wherein the control unit is configured to calculate a driving load amount of the driver based on the information relating to the changes in the traveling environment of the vehicle.

4. The sleepiness level prediction device of claim 1, wherein the control unit is configured to calculate the non-acclimation degree so that the non-acclimation degree has first order lag characteristics with respect to the change in the stimulus amount.

5. The sleepiness level prediction device of claim 1, wherein the control unit is configured to predict the sleepiness level of the driver after the prescribed time based on a state transition model in which a transition probability of transitioning from the current sleepiness level of the driver to the sleepiness level after the prescribed time is dependent on the non-acclimation degree calculated.

6. The sleepiness level prediction device of claim 5, wherein the control unit is configured to determine whether the sleepiness level of the driver after the prescribed time predicted previously matches the current sleepiness level of the driver estimated based on the information relating to the driver acquired by the driver information acquisition unit, and
    when the sleepiness level of the driver after the prescribed time predicted previously does not match the current sleepiness level, the control unit is configured to update the transition probability so that the sleepiness level of the driver after the prescribed time predicted previously matches the current sleepiness level.

7. The sleepiness level prediction device of claim 1, wherein the prescribed time includes a time period from implementation of sleepiness elimination control by the vehicle until exhibition of a suppression effect of sleepiness of the driver.

8. The sleepiness level prediction device of claim 1, wherein
    the vehicle information acquisition unit is configured to acquire, as the information relating to the vehicle, an information relating to a planned route along which the vehicle is planned to travel, and
    the control unit is configured to predict the predicted driving load after the prescribed time based on the information relating to the planned route.

9. A sleepiness level prediction method comprising:
    acquiring information relating to a vehicle;
    acquiring information relating to a driver;
    calculating a change in a stimulus amount given to the driver, the change in the stimulus amount being a difference between a current stimulus amount determined based on a current driving load of the driver and a predicted stimulus amount after a prescribed time determined based on a predicted driving load after the prescribed time, the predicted driving load being predicted based on the information relating to the vehicle, and calculating a non-acclimation degree indicative of a level at which the driver is not acclimated to driving based on the change in the stimulus amount; and
    predicting a sleepiness level of the driver after the prescribed time based on a current sleepiness level of the driver estimated based on the information relating to the driver and the non-acclimation degree.

* * * * *